United States Patent [19]
Hartwig et al.

[11] Patent Number: 5,977,361
[45] Date of Patent: *Nov. 2, 1999

[54] TRANSITION METAL-CATALYZED PROCESS FOR PREPARING N-ARYL COMPOUNDS

[75] Inventors: John F. Hartwig; Grace Mann, both of New Haven, Conn.

[73] Assignee: Yale University, New Haven, Conn.

[*] Notice: This patent issued on a continued prosecution application filed under 37 CFR 1.53(d), and is subject to the twenty year patent term provisions of 35 U.S.C. 154(a)(2).

[21] Appl. No.: 09/172,497

[22] Filed: Oct. 14, 1998

Related U.S. Application Data

[60] Provisional application No. 60/062,211, Oct. 16, 1997.

[51] Int. Cl.$^6$ .................................................. C07D 473/00
[52] U.S. Cl. .................... 544/264; 548/400; 548/300.1; 548/469; 548/360.1; 548/440; 548/356.1
[58] Field of Search .................... 544/264; 548/300.1, 548/360.1, 356.1, 400, 440, 469

[56] References Cited

U.S. PATENT DOCUMENTS

| | | | |
|---|---|---|---|
| 5,576,460 | 11/1996 | Buchwald et al. | 564/386 |
| 5,847,166 | 12/1998 | Buchwald et al. | 549/355 |

OTHER PUBLICATIONS

Evans, D.A. et al., Synthesis of Diaryl Ethers through the Copper–Promoted Arylation of Phenols with Arylboronic Acids. An Expedient Synthesis of Thyroxine; Tetrahedron Letters, vol. 39 (1998), pp. 2937–2940.

Wolfe, J.P. et al., An Ammonia Equivalent for the Palladium–Catalyzed Amination of Aryl Halides and Triflates; Tetrahedron Letters, vol. 38, No. 36 (1997) pp. 6367–6370.

Chan, D.M.T. et al., New N–and O–Arylations with Phenylboronic Acids and Cupric Acetate; Tetrahedron Letter, vol. 39 (1998) pp. 2933–2936.

Lam, P.Y.S. et al., New Aryl/Heteroaryl C–N Bond Cross–coupling Reactions via Arylboronic Acid/Cupric Acetate Arylation; Tetrahedron Letters, vol. 39 (1998) pp. 2941–2944.

Smith III, W.J. et al., A Novel and Selective Method for the N–Arylation of Indoles Mediated by $KF/Al_2O_3$; Tetrahedron Letters, vol. 37, No. 3 (1996) pp. 299–302.

Barton et al., Tetrahedron Letters., vol. 27, 1986: pp. 3615–3618.

Lopez–Alvarado et al., J. Org. Chem., 60, 1995 pp. 5678–5682.

Merck Index., 11th Edition p. 580 1983.

*Primary Examiner*—Richard L. Raymond
*Assistant Examiner*—Pavanaram K Sripada
*Attorney, Agent, or Firm*—Todd E. Garabedian; Wiggin & Dana

[57] ABSTRACT

The present invention is directed to a process for the preparation of N-aryl compounds containing at least one unsaturated nitrogen atom, comprising reacting a compound having at least one unsaturated nitrogen atom with an arylating compound in the presence of a base and a transition metal catalyst under reaction conditions effective to form an N-aryl compound containing at least one unsaturated nitrogen atom, wherein the aryl moiety of the N-aryl compound is bonded to the at least one unsaturated nitrogen atom, the transition metal catalyst comprising a Group 8 metal and at least one chelating ligand selected from the group consisting of Group 15-substituted metallocenes, Group 15-substituted arylenes, unsaturated Group 15 heterocycles, Group 15-substituted alkanes, and combinations thereof. The process of the present invention a useful general method of N-arylation for the manufacture of pharmaceuticals, polymers, and the like.

26 Claims, No Drawings

TRANSITION METAL-CATALYZED PROCESS FOR PREPARING N-ARYL COMPOUNDS

CROSS-REFERENCE TO RELATED APPLICATIONS

This application claims the benefit of U.S. Provisional Application No. 60/062,211 filed Oct. 16, 1997.

STATEMENT OF GOVERNMENT SUPPORT

This application was made with United States Government support under Award Number 1-R29-GM382-01 from the National Institutes of Health. The U.S. Government has certain rights in this invention.

BACKGROUND OF THE INVENTION

1. Field of the Invention

This invention relates to a general process for producing N-arylated compounds having at least one unsaturated nitrogen atom, and more particularly to a general process for the formation of N-arylated compounds from azoles or imines, and an arylating compound using a transition metal catalyst.

2. Description of the Art

N-Aryl azoles are important substructures in natural products and industrial chemicals, such as pharmaceuticals, dyes, and agricultural products. N-Aryl azoles such as N-aryl pyrrole, N-aryl carbazole, and N-aryl indole, display a variety of biological activity such as antimicrobial activity (Kamat et al., Ind. J. Chem., 33B:255–259 (1994)), dopamine D-2 and serotonin 5-HT2 antagonist activity (Perrgaard et al., J. Med. Chem. 35:1092–1101 (1992)); analgesic activity (Glamkowski et al., J. Med. Chem. 28:66–73 (1985) and antiallergy activity (Unangst et al., J. Med. Chem. 32:1360–1366 (1989)). N-Aryl imines, on the other hand, are protected anilines (Greene et al., Protective Groups in Organic Synthesis; John Wiley and Sons, Inc., New York, 1991) which are useful in the synthesis of pharmaceuticals, polymers and oligomers.

It would be advantageous to prepare N-aryl azoles and N-aryl imines from arylating compounds such as aryl halides and/or aryl sulfonates because aryl halides are generally inexpensive and readily available, while aryl sulfonates are easily prepared from phenols. However, to date, methods of producing N-aryl azoles an imines are inefficient or economically unattractive. In one example, the phenylation of azoles with electrophilic aromatic main group compounds produce N-aryl azoles as one of several aryl compounds in the resulting product mixture (Lopez-Alvarado et al., J. Org. Chem. 60:5678 (1995); Barton et al., Tetrahedron Lett. 27:3615–3618 (1986)). Complex purification steps are therefore required to isolate the desired compounds if this production method is used.

In another example, potassium fluoride adsorbed onto alumina mediates arylations of azoles with only electron-poor aryl halides (Smith III et al., Tetrahedron Lett. 37:299–302 (1996)). This method is inefficient with electron-rich aryl halides (e.g., 4-bromo-t-butyl benzene, 3-bromo-methoxy benzene, 2-bromo-toluene) and electron neutral aryl halides (e.g., bromobenzene). Thus, a variety of potentially useful arylating compounds cannot be utilized in this method.

In another example, copper-mediated arylation of azoles was demonstrated to require high temperatures and polar solvents, thus increasing the complexity of the reaction conditions (Khan et al., J. Chem. Soc. C, 85–91 (1970)). In yet another example, N-aryl azoles have been shown to be synthesized from aryl boronic reagents using copper catalysts (Chan et al., Tet. Lett. 39:2933–2936 (1998); Lam et al., Tet. Lett. 39:2941–2944 (1998)).

In view of the above, a need exists for a general and efficient process of synthesizing N-aryl azoles and N-aryl imines from readily available arylating compounds. The discovery and implementation of such a method would simplify the preparation of commercially significant organic N-aryl azoles and N-aryl imines and would enhance the development of novel polymers and pharmacologically active compounds. The present invention is believed to be an answer to that need.

SUMMARY OF THE INVENTION

In one aspect, the present invention is directed to a process for the preparation of N-aryl compounds containing at least one unsaturated nitrogen atom, comprising reacting a compound having at least one unsaturated nitrogen atom with an arylating compound in the presence of a base and a transition metal catalyst under reaction conditions effective to form an N-aryl compound containing at least one unsaturated nitrogen atom, wherein the aryl moiety of the N-aryl compound is bonded to the at least one unsaturated nitrogen atom, the transition metal catalyst comprising a Group 8 metal and at least one chelating ligand selected from the group consisting of Group 15-substituted metallocenes, Group 15-substituted arylenes, unsaturated Group 15 heterocycles, Group 15-substituted alkanes, and combinations thereof.

In another aspect, the present invention is directed to a process for the preparation of N-aryl compounds, comprising reacting a compound selected from the group consisting of azoles and imines with an arylating compound in the presence of a base selected from the group consisting of cesium carbonate and sodium tert-butoxide, and a transition metal catalyst selected from the group consisting of dichloro-[1,1'-bis(diphenylphosphino)-ferrocene]palladium (II), dichloro-[1,1'-bis(diphenylphosphino)-2,2'-binaphthyl]-palladium (II), under reaction conditions effective to form an N-arylated compound, wherein the aryl moiety of the N-arylated compound is bonded to an unsaturated nitrogen atom of the compound.

These and other aspects will become apparent upon reading the following detailed description of the invention.

DETAILED DESCRIPTION OF THE INVENTION

It now has been surprisingly found, in accordance with the present invention, that a solution is provided to the problem of providing a general and efficient process of synthesizing N-aryl compounds from a starting material having at least one unsaturated nitrogen atom, and an arylating compound. The present inventors have solved this problem by utilizing reaction conditions that include a base and a transition metal catalyst having a Group 8 metal and at least one chelating ligand selected from Group 15-substituted metallocenes, Group 15-substituted arylenes, unsaturated Group 15 heterocycles, Group 15-substituted alkanes, or combinations thereof. In one embodiment, the catalyst is represented by the formula:

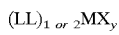

wherein (LL) is the chelating ligand, M is the Group 8 transition metal, each X is independently a monovalent anionic ligand, including, for example, a halide such as chloride or bromide; a carboxylate such as acetate; or an alkyl sulfonate such as triflate; or X is a divalent anionic ligand, such as carbonate; and wherein y represents the total number of anionic ligands X required to balance charge, typically from 0 to about 4. In one preferred embodiment, the catalyst comprises a palladium complex of 1,1'-bis (diphenylphosphino)-2,2'-binaphthyl (BINAP) or 1,1'-bis (diphenylphosphino)ferrocene (DPPF). The method of the present invention provides a general process for production of N-aryl azoles and N-aryl imines, two classes of compounds which are particularly significant in the development of pharmacologically active compounds and processing of polymers and oligomers.

As defined herein the terms "heterocycle" and "heterocyclic" refer to closed-ring structures, usually of either 5 or 6 members, in which at least a portion of the ring contains a carbon-nitrogen double bond, optionally in a resonance structure. The phrase "unsaturated nitrogen atom" refers to a carbon-nitrogen double bond, including carbon-nitrogen double bonds that are contained within an imine or a resonance structure of a heterocyclic compound. The term "aryl" is defined as a compound whose molecules have the ring structure characteristic of benzene, naphthalene, phenanthroline, anthracene, and the like. "Arylating compound" is defined as a compound which provides an aryl substituent in an organic reaction. "N-Aryl compounds" are those compounds in which an unsaturated nitrogen atom of the compound is substituted with an aryl group. "Ph" as defined herein is understood to represent a phenyl group.

The process of the present invention is directed to the synthesis of N-aryl compounds containing at least one unsaturated nitrogen atom, specifically N-aryl heterocyclic compounds (e.g., N-aryl azoles) and N-aryl imines where the aryl moiety is bonded to the unsaturated nitrogen atom. The process of the invention comprises reacting a compound having at least one unsaturated nitrogen atom with an arylating compound in the presence of a base and a transition metal catalyst under reaction conditions effective to form an N-aryl compound where the aryl moiety is bonded to the unsaturated nitrogen atom of the compound. The transition metal catalyst comprises a Group 8 metal and at least one chelating ligand selected from Group 15-substituted metallocenes, Group 15-substituted arylenes, unsaturated Group 15 heterocycles, Group 15-substituted alkanes, or combinations thereof.

More specifically, the process of this invention can be represented by Schemes Ia and Ib:

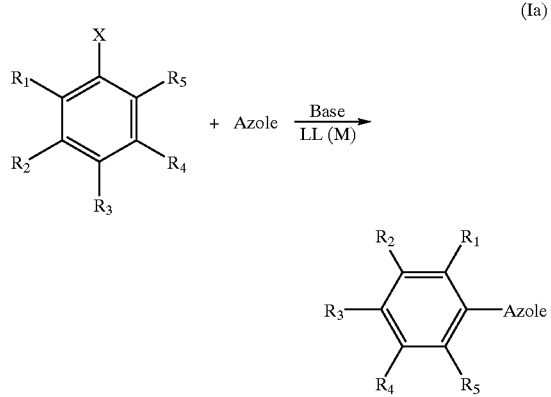

(Ia)

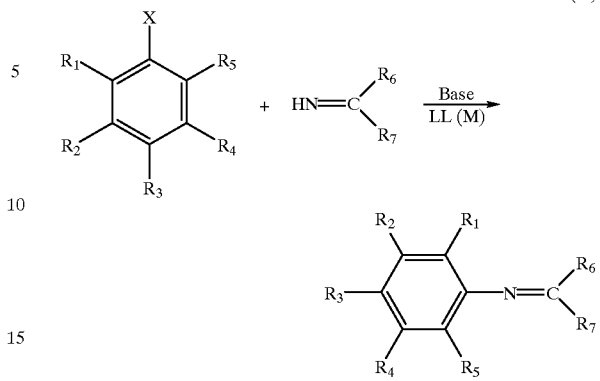

(Ib)

Briefly, in Scheme Ia, an arylating compound is reacted with an azole in the presence of a base, a chelating ligand (LL), and a Group 8 metal (M) to form an N-aryl azole compound. In Scheme Ib, an arylating compound is reacted with an imine in the presence of a base, a chelating ligand (LL), and a Group 8 metal (M) to form an N-aryl imine compound. Each of these reactions and their components are described in more detail below.

The arylating compound used in the process of the present invention may be any arylating compound of the formula (II):

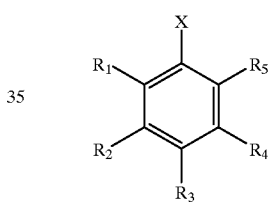

(II)

In formula II, X may be any halide atom (F, Cl, Br, I), or any sulfur-containing leaving group (e.g., triflate, sulfonate, tosylate, and the like) known in the art. Bromides are especially preferred in the process of the present invention. $R_1$, $R_2$, $R_3$, $R_4$, and $R_5$ are independently selected from H; CN; alkyl, such as methyl, ethyl, propyl, n-butyl, t-butyl, and the like; alkoxy, vinyl, alkenyl, formyl; $CF_3$; $CCl_3$; halide, $C_6H_5$; amide such as $C(O)N(CH_3)_2$, $C(O)N(CH_2CH_3)_2$, $C(O)N(CH_2CH_2CH_3)_2$, and the like; acyl, such as $C(O)$—$C_6H_5$, and the like; ester, amino, thioalkoxy, phosphino, and the like.

Preferred arylating compounds used in the process of the invention include include aryl bromides such as bromobenzene, 4-bromo-benzonitrile, 4-bromo-t-butyl benzene, 3-bromo-methoxy benzene, 2-bromo toluene, p-formyl phenyl bromide, p-$CF_3$ phenyl bromide, p-phenyl phenyl bromide, p-$C(O)N(CH_2CH_3)_2$ phenyl bromide, and p-$C(O)$—$C_6H_5$ phenyl bromide.

According to the method of the invention, compounds having at least one unsaturated nitrogen atom include, but are not limited to, heterocyclic compounds and imines.

Preferred heterocyclic compounds include azoles, such as pyrrole, indole, imidazole, benzimidazole, indazole, pyrazole, carbazole, purine, pyridine, and the like.

Imines useful in the process of the present invention have the formula

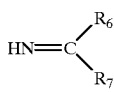

wherein R₆ and R₇ are independently selected from hydrogen, alkyl, phenyl, amino, dialkylamino, alkoxy, and combinations thereof. Preferably, R₆ and R₇ are each phenyl or dimethylamino, and more preferably, R₆ and R₇ are each phenyl. Particularly preferred imines are benzophenoneimine, guanidine, and tetramethyl guanidine.

The base shown in Schemes Ia and Ib is required for the process of the invention. Any base may be used so long as the process of the invention proceeds to the N-arylated product. It may be important in this regard that the base does not displace all of the chelating ligands on the catalyst. Nuclear magnetic resonance, infrared, and Raman spectroscopies, for example, are useful in determining whether the chelating ligands remain bonded to the Group 8 metal or whether the ligands have been displaced by the base.

Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethyl-ammonium hydroxide and tetraethylammonium hydroxide; and diaza organic bases, such as 1,8-diazabicyclo[5.4.0]-undec-7-ene and 1,8-diazabicyclo-[2.2.2.]-octane. Preferably, the base is an alkali hydroxide or alkali alkoxide, more preferably, an alkali alkoxide, and most preferably, an alkali metal $C_{1-10}$ alkoxide.

The quantity of base which is used can be any quantity which allows for the formation of the N-aryl product. Preferably, the molar ratio of base to arylating compound ranges from about 1:1 to about 3:1, and more preferably between about 1:1 and 2:1.

The catalyst, designated (LL)M in Schemes Ia and Ib, is characterized as comprising a metal atom or ion (M) and at least one or more chelating ligands (LL). The metal atom or ion is required to be a Group 8 transition metal, that is, a metal selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal.

The chelating ligand may be a neutral molecule or charged ion. A chelating ligand possesses a plurality of coordination sites, typically two, three, or four. Preferably, the chelating ligand is a bidentate ligand, that is, one having two coordination sites. The chelating ligand is also required to contain at least one element from Group 15 of the Periodic Table, preferably, at least one element of nitrogen, phosphorus, or arsenic, and more preferably nitrogen or phosphorus. If only one of the Group 15 elements is present, then at least a second chelating element is required, for example, oxygen or sulfur. More specifically, the chelating ligand is selected from the group consisting of Group 15-substituted arylenes, Group 15-substituted metallocenes, unsaturated Group 15 heterocycles, and Group 15-substituted alkanes.

The Term "Group 15-substituted arylenes" as used herein includes aromatic compounds substituted with at least one Group 15-containing moiety, preferably, at least one dialkyl or diaryl Group 15 moiety or hybrid thereof. The aromatic compound can be a single ring, fused ring, or multiple ring assembly. Other chelating elements, such as oxygen or sulfur, may be present. Non-limiting examples of Group 15-substituted arylenes which are chelating and beneficially employed in the process of this invention include 1,2-bis(diphenylphosphino)benzene, 1,1'-bis(diphenylphosphino)-2,2'-binaphthyl, 1-(dimethylarsino)-2-bis[(dimethylamino) phosphino]benzene, 1,2-bis(dimethylarsino)benzene, 5-10-dihydro-5,10-diphenyl-5-phospha-10-arsa-anthracene, 2-diphenylphosphino-N,N-dimethylaniline, 1,8-bis(diphenylphosphino)naphthalene, 2,2-bis(diphenylphosphino)diphenyl ether, 4,5-bis(diphenylphosphino)-9,9-dimethyl)xanthene, and 1,1'-bis(di-p-tolylphosphino)-2,2'-binaphthyl, 1-diphenylphosphino-1'-dimethylamino-2,2'-binaphthyl, 1-dicyclohexylphosphino-1'-dimethylamino-2,2'-binaphthyl, 1-di-t-butylphosphino-1'-dimethylamino-2,2'-binaphthyl, 1-di-i-propylphosphino-1'-dimethylamino-2,2'-binaphthyl, 1-diphenylphosphino-1'-methoxy-2,2'-binaphthyl, 1-dicyclohexylphosphino-1'-methoxy-2,2'-binaphthyl, 1-di-t-butylphosphino-1'-methoxy-2,2'-binaphthyl, 1-di-i-propylphosphino-1'-dimethylamino-2,2'-binaphthyl, 1-diphenylphosphino-1'-dimethylamino-2,2'-biphenyl, 1-dicyclohexylphosphino-1'-dimethylamino-2,2'-biphenyl, 1-di-t-butylphosphino-1'-dimethylamino-2,2'-biphenyl, 1-di-i-propylphosphino-1'-dimethylamino-2,2'-binaphthyl, 1-diphenylphosphino-1'-methoxy-2,2'-biphenyl, 1-dicyclohexylphosphino-1'-methoxy-2,2'-biphenyl, 1-di-t-butylphosphino-1'-methoxy-2,2'-biphenyl, 1-di-i-propylphosphino-1'-dimethylamino-2,2'-binaphthyl, 2-di-t-butylphosphinophenylethyl-di-t-butylphosphine, and 2-di-t-butylphosphinobenzyl-di-t-butylphosphine. Analogous diamino, diphosphino, and diarsino compounds and hybrids thereof are also suitable. Preferably, the Group 15-substituted arylene is a Group 15-substituted $C_{4-20}$ arylene, more preferably, a Group 15-substituted binaphthyl compound, more preferably, 1,1'-bis(diphenylphosphino)-2, 2'-binaphthyl (BINAP) or 1,1'-bis(di-p-tolyl-phosphino)-2, 2'-binaphthyl.

The term "Group 15-substituted metallocenes" as used herein includes metallocenes which are substituted with at least one Group 15-containing moiety, preferably at least one dialkyl or diaryl Group 15 moiety or hybrid thereof. Other chelating elements, for example, oxygen or sulfur, may be present. The metallocene itself comprises a transition metal atom or ion which is bonded to one or more $C_{4-8}$ multiply unsaturated hydrocarbon ring compounds. Suitable non-limiting examples of transition metal atoms in the metallocene include iron, titanium, vanadium, chromium, manganese, cobalt, nickel, molybdenum, and ruthenium. Preferably, the transition metal atom in the metallocene is iron. The $C_{4-8}$ multiply unsaturated hydrocarbon ring compounds suitably include cyclobutadiene, cyclopentadienyl, benzene, cycloheptatrienyl, and cyclooctatetraene. Representative metallocenes include ferrocene, ruthenocene, bis(benzene)chromium, bis(benzene)molybdenum, bis(benzene)tungsten, and cobaltocenium. Non-limiting examples of ligands which classify as chelating Group 15-substituted metallocenes include 1,1'bis(diphenylphosphino)ferrocene, 1-diphenylphosphino-2-(1-dimethylamino)ethyl ferrocene, 1-diphenylarsino-1'-diphenyl-phosphino ferrocene, 1-diphenylphosphino-2-(1-diphenylphosphino)ethyl ferrocene, 1-diphenylphosphino-2-(1-di-t-butylphosphino)ethyl ferrocene, 1-diphenylphosphino-2-(1-dicyclohexylphosphino)ethyl ferrocene, 1-dicyclohexylphosphino-2-(1-diphenylphosphino)ethyl ferrocene, 1-dicyclohexylphosphino-2-(1-dicyclohexylphosphino)ethyl ferrocene, 1-dicyclohexylphosphino-2-(1-dimethylamino)ethyl ferrocene, 1-di-t-butylphosphino-2-(1-dimethylamino)ethyl ferrocene, 1-di-i-propylphosphino-2-(1-dimethylamino)ethyl ferrocene, 1-diphenylphosphino-2-(1-dimethylamino)ethyl ferrocene, 1-[2-(diphenylphosphino)ferrocenyl]ethyl methyl ether, 1-[2-(dicyclohexylphosphino)ferrocenyl]ethyl methyl ether, 1-[2-(di-i-propylphosphino)ferrocenyl]ethyl methyl ether, 1-[2-(di-t-butylphosphino)ferrocenyl]ethyl methyl ether, (−)-(R)-N,N-dimethyl-1-[(S)-1',2-bis(diphenylphosphino)ferrocenyl]ethylamine, (+)-(S)-1-[(R)-2-(diphenylphosphino)ferrocenyl]ethyl methyl ether, and N,N-dimethyl-1,2-bis(di-t-butylphosphino)ferrocenyl]ethylamine. Analogous phosphine and amine substituted derivatives of the aforementioned metallocenes may also be employed. Preferably, the Group 15-substituted metallocene is a Group 15-substituted ferrocene, more preferably, 1,1'-bis(diphenylphos-phino)ferrocene (DPPF).

The term "unsaturated Group 15 heterocycles" as used herein includes any unsaturated single ring, multiple ring assembly, or fused ring system which comprises at least one Group 15 heteroatom. Preferably, the heteroatom is nitrogen. Chelating atoms outside of Group 15, such as oxygen or sulfur, may also be present. Non-limiting examples of unsaturated Group 15 heterocycles which are chelating and which can be beneficially employed in the process of the present invention include bipyridine, alkoxypyridine, imidazole, pyrazole, pyrimidine, pyridazine, purine, and quinazoline. Preferably, the unsaturated Group 15 heterocycle is an unsaturated $C_{5-15}$ Group 15 heterocycle, more preferably bipyridine or alkoxypyridine.

The term "Group 15-substituted alkanes" as used herein includes alkanes, preferably $C_{2-5}$ alkanes, and more preferably $C_{3-4}$ alkanes, which are substituted with at least one Group 15-containing moiety, preferably, a dialkyl or diaryl Group 15 moiety or hybrid thereof. Non-limiting examples of ligands which classify as chelating Group 15-substituted alkanes and which may be beneficially employed in the process of the present invention include 1,3-bis(diphenylphosphino)propane, 1,4-bis(diphenylphosphino)butane, 1,3-bis(diphenylarsino)propane, 1,4-bis(diphenylarsino)butane, 1-(diphenylphosphine)-2-(N,N-dimethyl)ethane, 1-(diphenyphosphino)-3-(N,N-dimethyl)propane, and 1-(diphenylarsino)-2-(diphenylphosphino)ethane.

In one preferred embodiment, the chelating ligand is a bidentate ligand containing at least one phosphorous atom. More preferably, the chelating ligand is a bidentate ligand selected from the group consisting of phosphorous-substituted arylenes and phosphorous-substituted metallocenes. Most preferably, the ligand is 1,1'-bis(diphenylphosphino)-2,2'-binapthyl (BINAP), 1,1'-bis(di-p-tolylphosphino)-2,2'-binapthyl(Tol-BINAP), or 1,1'-bis(diphenylphosphino)ferrocene (DPPF).

Many of the aforementioned metal catalysts which are beneficially employed in the process of this invention can be represented by the following formula:

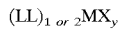

wherein (LL) is the chelating ligand, M is the Group 8 transition metal, each X is independently a monovalent anionic ligand, including for example a halide, such as chloride or bromide; a carboxylate, such as acetate; or an alkyl sulfonate, such as triflate; or X is a divalent anionic ligand, such as sulfonate or carbonate; and wherein y represents the total number of anionic ligands X required to balance charge, typically from 0 to about 4. It is to be understood that any of the chelating ligands described earlier may be used in the above formula. Non-limiting examples of suitable transition metal complexes include dichloro-[1,1'-bis(diphenylphosphino)ferrocene]palladium (II). dichloro-[1,1'-bis(diphenylphosphino)-2,2'-binapthyl]palladium (II), dichloro-[1,2-bis(diphenylarsino)benzene]platinum (II), 1,2-bis[(diphenylphosphino)benzene]platinum (II) acetate, dichloro-[1-diphenylphosphino-2-(1-dimethylamino) ethylferrocene]palladium (II), and analogous complexes containing bidentate ligands mentioned hereinbefore with iron, cobalt, nickel, ruthenium, rhodium, osmium, and iridium as the metal component.

Methods for preparing the aforementioned catalysts are known to those skilled in the art. For a description of general synthetic techniques, see *Inorganic Synthesis: Reagents for Transition Metal Complex and Organometallic Systems*; R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

Heretofore, the transition metal catalyst has been described as comprising a transition metal and a chelating ligand. It is not precisely known, however, whether both, one, or neither donor atoms of the chelating ligand are bound to the transition metal during the entire process of this invention or whether the chelating ligand is in a labile or non-bonded configuration relative to the transition metal during part or all of the process. Generally, it is believed that the chelating ligand is bonded through the Group 15 element to the transition metal; however, such a theory should not be binding upon the invention in any manner. Modern analytical techniques, such as nuclear magnetic resonance spectroscopy ($^{13}C$, $^1H$, $^{31}P$), infrared and Raman spectroscopies, and X-ray diffraction, may assist in the determination of initial catalyst structure and changes in structure throughout the process.

The transition metal catalyst may be synthesized first and thereafter employed in the arylation process. Alternatively, the catalyst can be prepared in situ in the arylation reaction mixture. If the latter mixture is employed, then a Group 8 catalyst precursor compound and the desired chelating ligand are independently added to the reaction mixture wherein formation of the transition metal catalyst occurs in situ. Suitable precursor compounds include alkene and diene complexes of the Group 8 metals, preferably, di(benzylidene)acetone (dba) complexes of the Group 8 metals, as well as, monodentate phosphine complexes of the Group 8 metals, and Group 8 carboxylates. In the presence of the chelating ligand, such as DPPF or BINAP, in situ formation of the transition metal catalyst occurs. Non-limiting examples of suitable precursor compounds include [bis-di(benzylidene)acetone]palladium (0), tetrakis-(triphenylphosphine)-palladium (0), tris-[di(benzylidene) acetone]palladium (0), tris-[di(benzylidene)acetone]-dipalladium (0), palladium acetate, and the analogous complexes of iron, cobalt, nickel, ruthenium, rhodium, osmium, iridium, and platinum. Any of the aforementioned catalyst precursors may include a solvent of crystallization.

Group 8 metals supported on carbon, preferably, palladium on carbon, can also be suitably employed as a precursor compound. Preferably, the catalyst precursor compound is bis-[di(benzylidene)acetone]palladium(0).

The quantity of transition metal catalyst which is employed in the process of this invention is any quantity which promotes the formation of the N-aryl product. Generally, the quantity is a catalytic amount, which means that the catalyst is used in an amount which is less than stoichiometric relative to the unsaturated organic sulfonate. Typically, the transition metal catalyst ranges from about 0.01 to about 20 mole percent, based on the number of moles of the compound having at least one unsaturated nitrogen atom used in the reaction. Preferably, the quantity of transition metal catalyst ranges from about 1 to about 10 mole percent, and more preferably from about 3 to about 8 mole percent, based on the moles of the unsaturated nitrogen-containing compound.

The process described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the compound having at least one unsaturated nitrogen atom, arylating compound, base, and catalyst are mixed in batch, optionally with a solvent, and the resulting mixture is maintained at a temperature and pressure effective to prepare the N-arylated product.

Any solvent can be used in the process of the invention provided that it does not interfere with the formation of the N-aryl product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydrofuran. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed together or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired N-aryl product. Beneficially, the reaction conditions for this process are mild. For example, a preferred temperature for the process of the present invention ranges from about ambient, taken as about 22° C., to about 150° C., and preferably, from about 80° C. to about 110° C. The process may be run at subatmospheric pressures if necessary, but typically proceeds sufficiently well at about atmospheric pressure. The process is generally run for a time sufficient to convert as much of the unsaturated nitrogen-containing compound to product as possible. Typical reaction times range from about 30 minutes to about 24 hours, but longer times may be used if necessary.

The heterocyclic N-arylated product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of N-aryl product recovered, based on the number of moles of unsaturated nitrogen-containing compound employed. Typically, the yield of N-aryl product is greater than about 25 mole percent. Preferably, the yield of N-aryl product is greater than about 60 mole percent, and more preferably, greater than about 80 mole percent.

The following examples are intended to illustrate, but in no way limit the scope of the present invention. All parts and percentages are by weight and all temperatures are in degrees Celsius unless explicitly stated otherwise.

EXAMPLES 1–12

The results of twelve (12) N-arylation reactions are shown in Table I. As indicated in Table I, each N-arylation reaction was undertaken using one of four methods, each of which is described in more detail below. Yields are for isolated pure material and are an average of at least two runs.

Method A: 1.2 mmol of aryl halide (ArBr), 1.0 mmol of azole, 1.2 mmol $Cs_2CO_3$ as the base, 1 mol % of $Pd(OAc)_2$, and 1.5 mol % of 1,1'-bis(diphenylphosphino)ferrocene (DPPF) were reacted by mixing with a magnetic stir bar at 100° C. for 12 hours. The reactions were conducted in toluene solvent, and the products were isolated by silica gel chromatograph using hexanes and ethyl acetate (EtOAc) using procedures well known in the art.

Method B: Procedures are the same as Method A, except 1.5 mmol aryl halide, 1.5 mmol NaO-t-Bu as base, 5.0 mol % $Pd(OAc)_2$, 6.0 mol % DPPF were reacted at 120° C. for 48 hours. Solvent and isolation procedure was the same as Method A.

Method C: Procedures are the same as Method A, except 1.2 mmol NaO-t-Bu, 0.5 mol % $Pd(OAc)_2$, and 0.75 mol % DPPF were reacted at 100° C. for 12 hours. Solvent and isolation procedure was the same as Method A.

Method D: Procedures are the same as Method A, except 19.2 μmol aryl halide, 4.7 μmol azole, 8 mmol tol-BINAP, 12.1 μmol NaOH as base, and 1.4 μmol $Pd(OAc)_2$ were reacted at 120° C. for 12 hours. Solvent and isolation procedure was the same as Method A. The product was quantified by gas chromatography of the crude reaction solution.

TABLE I

| Example | Azole or Imine | Arylating Compound BrC$_6$H$_5$R R = | Product | Method | Yield (%) |
|---|---|---|---|---|---|
| 1 | Pyrrole | p-CN | NC–C$_6$H$_4$–pyrrole | A | 92 |
| 2 | Pyrrole | p-t-Bu | tBu–C$_6$H$_4$–pyrrole | B | 87 |
| 3 | Pyrrole | m-OMe | MeO–C$_6$H$_4$–pyrrole | B | 74 |
| 4 | Pyrrole | o-Me | Me–C$_6$H$_4$–pyrrole | B | 25 |
| 5 | Carbazole | p-CN | NC–C$_6$H$_4$–carbazole | A | 97 |
| 6 | Indole | p-CN | NC–C$_6$H$_4$–indole | A | 98 |
| 7 | Indole | p-C(O)H | OHC–C$_6$H$_4$–indole | A | 76[a] |
| 8 | Indole | p-CF$_3$ | F$_3$C–C$_6$H$_4$–indole | A | 90[b] |
| 9 | Indole | p-Ph | Ph–C$_6$H$_4$–indole | A | 72 |

TABLE I-continued

| Example | Azole or Imine | Arylating Compound BrC$_6$H$_5$R R = | Product | Method | Yield (%) |
|---|---|---|---|---|---|
| 10 | Indole | p-C(O)NEt$_2$ | 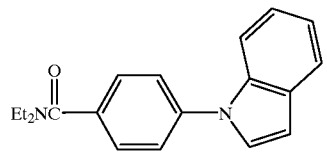 | A | 85 |
| 11 | Indole | p-H | 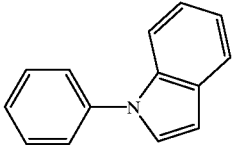 | B | 78 |
| 12 | HN=C(Ph)$_2$ | p-CN | 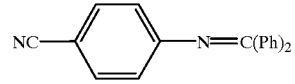 | C | 92 |
| 13 | HN=C(Ph)$_2$ | o-OMe | 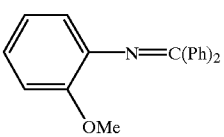 | C | 86 |
| 14 | HN=C(Ph)$_2$ | o-Me | 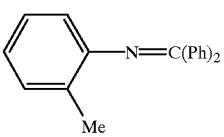 | C | 90 |
| 15 | HN=C(Ph)$_2$ | p-OMe | 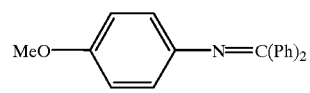 | C | 93 |
| 16 | HN=C(Ph)$_2$ | p-C(O)Ph | 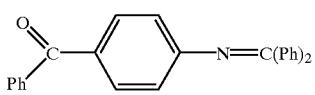 | C | 90 |
| 17 | Pyridine | p-t-Bu | 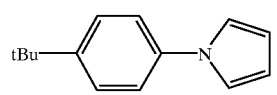 | D | 64 | aProduct discolored after a day at room temperature.
bYield reported by gas chromatography analysis.

As shown in Table I, the combination of Pd(OAc)$_2$ and either DPPF or tol-BINAP catalyzed the formation of N-aryl azoles or N-aryl imines in the presence of Cs$_2$CO$_3$ or NaO-t-Bu or NaOH with electron rich aryl halides (examples 2, 3, and 4), electron neutral aryl halides (example 11), or electron poor aryl halides (examples 1, and 5–10). Reactions of electron rich aryl halides required slightly higher temperatures and longer reaction times than reactions of electron poor aryl halides.

The rate for reductive elimination of potential azolyl intermediates was observed to be more efficient if a chelating phosphine and a base that generates only small amount of pyrrolyl anion is used. It was observed that anionic PPh$_3$ complexes reacted at 120° C. to give Pd(0), but gave N-aryl pyrrole in only about 8% yield. The neutral PPh$_3$ complexes also formed Pd(0) at 120° C. but produced N-aryl azole in a modest yield of 20%. These results contrast the high-yielding reductive eliminations of arylamines under mild conditions from analogous PPh$_3$-ligated amido aryl complexes and show that the coupling reaction form a C—N bond between an aryl and a nitrogen-bound heteroaromatic ligand is more difficult than the formation of a C—N bond between an aryl group and an amide.

In contrast to the PPh$_3$ pyrrolyl complexes, DPPF-ligated palladium pyrrolyl aryl complexes reductively eliminated N-aryl pyrrole in high yields, demonstrating that there are palladium complexes that can form this type of C—N bond and that chelating phosphines are important to observe this reductive elimination. Anionic DPPF complexes undergo reductive elimination in 15 h at 120° C. in about 40% yield, while neutral DPPF complexes undergo reductive elimination in about 90% yield. It is, therefore, important to discourage or reduce formation of the anionic pyrrolyl complexes in catalytic reactions. Indeed, the catalytic reaction of 4-bromo-t-butylbenzene with sodium pyrrolyl catalyzed by DPPF-palladium occurred in 29% yield, significantly lower than the reactions of aryl bromide with pyrrole and alkoxide or carbonate base.

In addition to catalyzing the arylation of azoles, the combination of Pd(OAc)$_2$ and DPPF catalyzed the arylation of benzophenone imine (examples 12–16), which contains an Sp$^2$-hybridized nitrogen with a more basic electron pair.

This imine arylation reaction is general for electron poor, electron rich, and sterically hindered aryl halides. In general, the arylations of benzophenone imine occurred at lower temperatures and shorter times than the arylations of azoles. For reactions of electron neutral aryl halides, NaO-t-Bu was a superior base to CS$_2$CO$_3$.

Palladium aryl methyleneamido intermediate complexes could be generated in high yield and characterized by solution $^1$H and $^{31}$P NMR spectrometry, as well as IR spectroscopy. Reaction of KN=CPh$_2$ with (DPPF)Pd (C$_6$H$_4$-t-Bu) (Br) formed (DPPF)Pd(C$_6$H$_4$-t-Bu) (N=CPh$_2$) cleanly at room temperature. Alternatively, this intermediate complex was generated in high yield by reaction of HN=CPh$_2$) (DPPF)Pd(C$_6$H$_4$-t-Bu) (O-t-Bu) (Mann et al., J. Am. Chem. Soc., 118:12109 (1996)).

Methyleneamido intermediate complexes undergo reductive elimination of N-arylimine in quantitative yield in less than an hour at room temperature. This observation confirmed the solution structural assignment of several intermediates and demonstrated a large difference in reductive elimination rates for the two complexes with sp$^2$-hybridized, aromatic or unsaturated nitrogen centers bound to the palladium. The rate for reductive elimination of the N-aryl imine is more similar to the rates of C—N bond-forming reductive elimination of arylamines of C—C bond-forming reductive elimination of styrenes than it is to the C—N(Sp$^2$) bond-forming reductive elimination of N-aryl azoles.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents, patent applications, and publications mentioned herein are incorporated by reference in their entireties.

What is claimed is:

1. A process for the preparation of N-aryl compounds containing at least one unsaturated nitrogen atom, comprising reacting a compound having at least one unsaturated nitrogen atom with an arylating compound in the presence of a base and a transition metal catalyst under reaction conditions effective to form an N-aryl compound containing at least one unsaturated nitrogen atom, wherein the aryl moiety of said N-aryl compound is bonded to said at least one unsaturated nitrogen atom, said transition metal catalyst comprising a Group 8 metal and at least one chelating ligand selected from the group consisting of Group 15-substituted metallocenes, Group 15-substituted arylenes, unsaturated Group 15 heterocycles, Group 15-substituted alkanes, and combinations thereof.

2. The process of claim 1, wherein said compound having at least one unsaturated nitrogen atom is selected from the group consisting of heterocyclic compounds, imines, and combinations thereof.

3. The process of claim 2, wherein said heterocyclic compound is an azole.

4. The process of claim 3, wherein said azole is selected from the group consisting of pyrrole, indole, imidazole, benzimidazole, indazole, pyrazole, carbazole, purine, and combinations thereof.

5. The process of claim 2, wherein said imine is selected from those having the formula

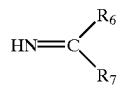

wherein R$_6$ and R$_7$ are independently selected from the group consisting of hydrogen, alkyl, phenyl, amino, dialkylamino, alkoxy, and combinations thereof.

6. The process of claim 1, wherein said arylating compound is selected from those having the formula

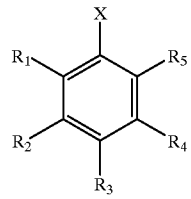

wherein X is a halogen atom or a sulfur-containing leaving group, and R$_1$, R$_2$, R$_3$, R$_4$, R$_5$ are independently selected from the group consisting of H, CN, alkyl, alkoxy, vinyl, alkenyl, formyl, CF$_3$, CCl$_3$, halide, C$_6$H$_5$, amide, acyl, ester, alkoxy, amino, thioalkoxy, phosphino, and combinations thereof.

7. The process of claim 6, wherein said sulfur-containing leaving group is selected from the group consisting of sulfonate, triflate, tosylate, and combinations thereof.

8. The process of claim 6, wherein said arylating compound is selected from those having the formula BrC$_6$H$_5$R, wherein R is selected from the group consisting of p-CN, p-t-Bu, m-OMe, o-Me, p-C(O)H, p-CF$_3$, p-Ph, p-C(O)Et$_2$, p-H, and p-C(O)Ph.

9. The process of claim 1, wherein said base is selected from the group consisting of alkali metal hydroxides, alkali metal alkoxides, metal carbonates, alkali metal amides, alkali metal aryl oxides, tertiary amines, tetraalkylammonium hydroxides, diaza organic bases, and combinations thereof.

10. The process of claim 1, wherein said Group 8 metal is palladium, platinum, or nickel.

11. The process of claim 1, wherein said Group 15-substituted metallocene is a Group 15-substituted metallocene of iron, titanium, vanadium, chromium, manganese, cobalt, nickel, molybdenum, or ruthenium.

12. The process of claim 11, wherein said Group 15-substituted metallocene is a Group 15-substituted ferrocene.

13. The process of claim 12, wherein said Group 15-substituted ferrocene is 1,1'-bis(diphenylphosphino) ferrocene (DPPF).

14. The process of claim 1, wherein said Group 15-substituted arylene is a Group 15-substituted $C_{4-20}$ arylene.

15. The process of claim 14, wherein the Group 15-substituted arylene is 1,1'-bis(diphenylphosphino)-2,2'-binaphthyl (BINAP) or 1,1'-bis(di-p-tolylphosphino)-2,2'-binaphthyl (Tol-BINAP).

16. The process of claim 1, wherein said transition metal catalyst has the formula $$(LL)_{1 \text{ or } 2}MX_y$$

wherein (LL) is the chelating ligand, M is the Group 8 transition metal, each X is independently a monovalent or divalent anionic ligand, and wherein y varies from 0 to 4.

17. The process of claim 16, wherein the transition metal catalyst is selected from the group consisting of dichloro-[1,1'-bis(diphenylphosphino)-ferrocene]palladium (II), dichloro-[1,1-bis(diphenylphosphino)-2,2'-binaphthyl]-palladium (II), dichloro-[1,2-bis(diphenyl-arsino)benzene] platinum (II), 1,2-bis(diphenylphos-phino)benzene) platinum (II) acetate, dichloro-[1-diphenylphosphino-2-(1-dimethylamino)ethyl-ferrocene]palladium (II), and combinations thereof.

18. The process of claim 1, wherein said transition metal catalyst is prepared in situ in the reaction mixture.

19. The process of claim 18, wherein said transition metal catalyst is prepared from an alkene or diene complex of a Group 8 transition metal complex or a Group 8 transition metal carboxylate combined with 1,1'-bis(diphenylphosphino)ferrocene or 1,1'-bis(diphenylphosphino)-2,2-binaphthyl.

20. The process of claim 19, wherein the alkene complex of the Group 8 transition metal is di(benzylidene)acetone.

21. The process of claim 1, wherein said transition metal catalyst is anchored or supported on a support.

22. The process of claim 1, wherein said reaction conditions further comprise a solvent selected from the group consisting of aromatic hydrocarbons, chlorinated aromatic hydrocarbons, ethers, water, aliphatic alcohols, and combinations thereof.

23. The process of claim 1, further comprising the step of isolating said N-aryl compounds.

24. A process for the preparation of N-aryl compounds, comprising reacting a compound selected from the group consisting of azoles and imines with an arylating compound in the presence of a base selected from the group consisting of cesium carbonate and sodium tert-butoxide, and a transition metal catalyst selected from the group consisting of dichloro-[1,1'-bis(diphenylphosphino)-ferrocene]palladium (II), dichloro-[1,1-bis(diphenylphosphino)-2,2'-binaphthyl]-palladium (II), under reaction conditions effective to form an N-arylated compound, wherein the aryl moiety of said N-arylated compound is bonded to an unsaturated nitrogen atom of said compound.

25. The process of claim 24, wherein said azole is selected from the group consisting of pyrrole, indole, imidazole, benzimidazole, indazole, pyrazole, carbazole, purine, and combinations thereof.

26. The process of claim 24, wherein said imine is selected from those having the formula

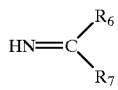

wherein $R_6$ and $R_7$ are independently selected from the group consisting of hydrogen, alkyl, phenyl, amino, dialkylamino, alkoxy, and combinations thereof.

* * * * *

UNITED STATES PATENT AND TRADEMARK OFFICE
CERTIFICATE OF CORRECTION

| | | |
|---|---|---|
| PATENT NO. | : 5,977,361 | Page 1 of 1 |
| APPLICATION NO. | : 09/172497 | |
| DATED | : November 2, 1999 | |
| INVENTOR(S) | : John F. Hartwig et al. | |

It is certified that error appears in the above-identified patent and that said Letters Patent is hereby corrected as shown below:

Column 1, line 12, "Award Number 1-R29-GM382-01" should be changed to -- Grant Number GM038201 --

Signed and Sealed this

Eighteenth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 5,977,361 | Page 1 of 1 |
| APPLICATION NO. | : 09/172497 | |
| DATED | : November 2, 1999 | |
| INVENTOR(S) | : John F. Hartwig et al. | |

It is certified that error appears in the above-identified patent and that said Letters Patent is hereby corrected as shown below:

Column 1, line 12, delete the text under the heading "STATEMENT OF GOVERNMENT SUPPORT" as in the original patent and corrected by a previous certificate of correction and replace with the following:

---This invention was made with government support under GM038201 awarded by National Institutes of Health. The government has certain rights in the invention.---

Signed and Sealed this
Seventeenth Day of May, 2016

Michelle K. Lee
*Director of the United States Patent and Trademark Office*